(12) United States Patent
Silver

(10) Patent No.: US 9,828,337 B2
(45) Date of Patent: *Nov. 28, 2017

(54) LYSINE DERIVATIVE HAVING AN ISOTHIOCYANATE FUNCTIONAL GROUP AND ASSOCIATED METHOD OF USE

(71) Applicant: Michael E. Silver, Holland, MI (US)

(72) Inventor: Michael E. Silver, Holland, MI (US)

(73) Assignee: The William M. Yarbrough Foundation, Peoria, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/880,408

(22) Filed: Oct. 12, 2015

(65) Prior Publication Data

US 2016/0030379 A1 Feb. 4, 2016

Related U.S. Application Data

(63) Continuation of application No. 14/594,788, filed on Jan. 12, 2015, which is a continuation of application No. 13/342,516, filed on Jan. 3, 2012, now Pat. No. 8,933,119.

(60) Provisional application No. 61/429,325, filed on Jan. 3, 2011, provisional application No. 61/502,067, filed on Jun. 28, 2011.

(51) Int. Cl.
| | | |
|---|---|---|
| *C07C 331/20* | (2006.01) |
| *A61K 31/26* | (2006.01) |
| *A61P 17/00* | (2006.01) |
| *A61K 9/00* | (2006.01) |
| *A61K 31/145* | (2006.01) |
| *A61K 31/198* | (2006.01) |
| *A61K 45/06* | (2006.01) |
| *A61K 47/34* | (2017.01) |

(52) U.S. Cl.
CPC .......... *C07C 331/20* (2013.01); *A61K 9/0014* (2013.01); *A61K 31/145* (2013.01); *A61K 31/198* (2013.01); *A61K 31/26* (2013.01); *A61K 45/06* (2013.01); *A61K 47/34* (2013.01)

(58) Field of Classification Search
CPC .. A61K 31/145; A61K 9/0014; A61K 31/198; A61K 45/06; A61K 47/34; A61K 31/26; C07C 331/20
USPC ............... 514/514, 562, 563, 625, 663, 665; 558/17
See application file for complete search history.

(56) References Cited

U.S. PATENT DOCUMENTS

| | | |
|---|---|---|
| 2,905,701 A | 9/1959 | Nutting et al. |
| 3,108,040 A | 10/1963 | Folkers |
| 3,725,030 A | 4/1973 | Newallis et al. |
| 3,740,435 A | 6/1973 | Newallis et al. |
| 3,969,087 A | 7/1976 | Saito et al. |
| 4,083,836 A | 4/1978 | Anjou et al. |
| 4,158,656 A | 6/1979 | Jones et al. |
| 4,191,752 A | 3/1980 | Kada et al. |
| 4,938,949 A | 7/1990 | Borch et al. |
| 5,114,969 A | 5/1992 | Chung et al. |
| 5,126,129 A | 6/1992 | Wiltrout et al. |
| 5,208,249 A | 5/1993 | Rowe et al. |
| 5,231,209 A | 7/1993 | Chung et al. |
| 5,290,578 A | 3/1994 | Passey et al. |
| 5,385,734 A | 1/1995 | Friedman |
| 5,411,986 A | 5/1995 | Cho et al. |
| 5,582,818 A | 12/1996 | Nakanishi et al. |
| 5,589,504 A | 12/1996 | Dannenberg et al. |
| 5,686,108 A | 11/1997 | Pusateri et al. |
| 5,725,895 A | 3/1998 | Fahey et al. |
| 5,882,646 A | 3/1999 | Pusateri et al. |
| 5,968,505 A | 10/1999 | Fahey et al. |
| 5,968,567 A | 10/1999 | Fahey et al. |
| 6,008,260 A | 12/1999 | Pezzuto et al. |
| 6,046,231 A | 4/2000 | Kosmeder, II et al. |
| RE36,784 E | 7/2000 | Cho et al. |
| 6,166,003 A | 12/2000 | Lam |
| 6,172,250 B1 | 1/2001 | Seguin et al. |
| 6,177,122 B1 | 1/2001 | Fahey et al. |
| 6,242,018 B1 | 6/2001 | Fahey et al. |
| 6,340,784 B1 | 1/2002 | Mithen et al. |
| 6,348,220 B1 | 2/2002 | Ribnicky et al. |
| 6,414,037 B1 | 7/2002 | Pezzuto et al. |
| 6,436,450 B1 | 8/2002 | Omary et al. |
| 6,455,554 B1 | 9/2002 | Dull et al. |
| 6,465,512 B2 | 10/2002 | Nakamura et al. |
| 6,492,399 B1 | 12/2002 | Dull et al. |
| 6,524,594 B1 | 5/2003 | Santora et al. |
| 6,680,062 B2 | 1/2004 | Muizzuddin et al. |

(Continued)

FOREIGN PATENT DOCUMENTS

| | | |
|---|---|---|
| CN | 101091705 | 12/2007 |
| EP | 0998943 | 5/2000 |

(Continued)

OTHER PUBLICATIONS

Saint-Mezard et al. Eur. J. Dermatol. 2004, 14, 284-295.*

(Continued)

*Primary Examiner* — Irina Neagu

(74) *Attorney, Agent, or Firm* — King & Partners, PLC

(57) ABSTRACT

A method for treating phytophotodermatitis including the steps of applying an isothiocyanate functional surfactant to an area affected by phytophotodermatitis, wherein said isothiocyanate functional surfactant comprises at least one isothiocyanate functional group associated with an aliphatic and/or aromatic carbon atom of the isothiocyanate functional surfactant.

8 Claims, No Drawings

(56) References Cited

U.S. PATENT DOCUMENTS

| | | | |
|---|---|---|---|
| 6,737,441 B2 | 5/2004 | Fahey | |
| 6,824,796 B2 | 11/2004 | Pusateri et al. | |
| 6,878,751 B1 | 4/2005 | Donnelly et al. | |
| 6,991,811 B1 | 1/2006 | Brovelli et al. | |
| 7,303,770 B2 | 12/2007 | Fahey et al. | |
| 7,402,569 B2 | 7/2008 | Fahey | |
| 7,407,986 B2 | 8/2008 | Gao et al. | |
| 7,615,657 B2 | 11/2009 | Bathurst et al. | |
| 7,744,937 B2 | 6/2010 | West et al. | |
| 7,820,145 B2 | 10/2010 | Tamarkin et al. | |
| 7,879,822 B2 | 1/2011 | Dagan et al. | |
| 8,003,633 B1 | 8/2011 | Robertson et al. | |
| 8,008,281 B2 | 8/2011 | Prendergast et al. | |
| 8,039,511 B2 | 10/2011 | Cheng et al. | |
| 8,158,161 B2 | 4/2012 | Sussan et al. | |
| 8,168,655 B2 | 5/2012 | Gadek et al. | |
| 8,303,949 B2 | 11/2012 | Gao et al. | |
| 8,309,541 B1 | 11/2012 | Robertson et al. | |
| 8,410,037 B2 | 4/2013 | Molenda et al. | |
| 8,492,616 B2 | 7/2013 | Mero | |
| 8,510,127 B2 | 8/2013 | Hermann et al. | |
| 8,709,406 B2 | 4/2014 | Gao et al. | |
| 8,731,970 B2 | 5/2014 | Hermann et al. | |
| 8,772,251 B2 | 7/2014 | Morazzoni et al. | |
| 8,772,274 B1 | 7/2014 | Robertson et al. | |
| 8,835,721 B2 | 9/2014 | Mero | |
| 8,865,765 B2 * | 10/2014 | Silver | A61K 31/26 514/506 |
| 8,865,772 B2 | 10/2014 | Silver | |
| 8,921,644 B2 | 12/2014 | Barten | |
| 8,933,119 B2 * | 1/2015 | Silver | A61K 9/0014 514/514 |
| 9,017,666 B2 | 4/2015 | Ashurst | |
| 9,096,505 B2 | 8/2015 | Robertson et al. | |
| 9,096,611 B2 | 8/2015 | Ren et al. | |
| 9,126,910 B2 | 9/2015 | Robertson et al. | |
| 9,126,911 B2 | 9/2015 | Robertson et al. | |
| 9,131,722 B2 | 9/2015 | Kim et al. | |
| 9,181,221 B2 | 11/2015 | Ren et al. | |
| 9,254,331 B2 | 2/2016 | Dubois et al. | |
| 9,308,192 B2 | 4/2016 | Coulombe et al. | |
| 9,315,505 B2 | 4/2016 | Ren et al. | |
| 9,359,349 B2 | 6/2016 | Ren et al. | |
| 9,393,225 B2 | 7/2016 | Beumer et al. | |
| 2002/0164381 A1 | 11/2002 | Shacknai et al. | |
| 2003/0185864 A1 | 10/2003 | Kobayashi et al. | |
| 2003/0198616 A1 | 10/2003 | Howard | |
| 2004/0156873 A1 | 8/2004 | Gupta | |
| 2005/0042182 A1 | 2/2005 | Arkin et al. | |
| 2005/0095261 A1 | 5/2005 | Popp | |
| 2005/0100621 A1 | 5/2005 | Popp et al. | |
| 2005/0118124 A1 | 6/2005 | Reinhart et al. | |
| 2005/0193448 A1 | 9/2005 | Gardner et al. | |
| 2006/0127996 A1 | 6/2006 | Fahey | |
| 2006/0160713 A1 | 7/2006 | Sekine et al. | |
| 2007/0041925 A1 | 2/2007 | Picano et al. | |
| 2008/0154210 A1 | 6/2008 | Jordan et al. | |
| 2008/0254150 A1 | 10/2008 | Rheins et al. | |
| 2008/0306148 A1 | 12/2008 | Robertson et al. | |
| 2008/0311192 A1 | 12/2008 | West et al. | |
| 2008/0311276 A1 | 12/2008 | West et al. | |
| 2009/0081138 A1 | 3/2009 | Ashurst | |
| 2009/0186853 A1 | 7/2009 | Yu et al. | |
| 2009/0324522 A1 | 12/2009 | Chevreau | |
| 2010/0124598 A1 | 5/2010 | West et al. | |
| 2011/0003747 A1 | 1/2011 | Coloumbe et al. | |
| 2011/0014137 A1 | 1/2011 | Talalay et al. | |
| 2011/0028548 A1 | 2/2011 | Fossel | |
| 2011/0195103 A1 | 8/2011 | Perez Arcas et al. | |
| 2012/0202878 A1 | 8/2012 | Silver | |
| 2013/0116203 A1 | 5/2013 | Rajski et al. | |
| 2014/0075590 A1 | 3/2014 | Van Den Bosch et al. | |
| 2015/0038579 A1 * | 2/2015 | Silver | A61K 31/26 514/514 |
| 2015/0126600 A1 * | 5/2015 | Silver | A61K 9/0014 514/514 |
| 2016/0015676 A1 * | 1/2016 | Silver | A61K 31/26 514/514 |
| 2016/0015677 A1 * | 1/2016 | Silver | A61K 31/26 514/514 |
| 2016/0022624 A1 * | 1/2016 | Silver | A61K 31/26 514/514 |
| 2016/0030379 A1 | 2/2016 | Silver | |
| 2016/0030380 A1 * | 2/2016 | Silver | A61K 9/0014 514/514 |
| 2016/0030381 A1 * | 2/2016 | Silver | A61K 9/0014 514/514 |

FOREIGN PATENT DOCUMENTS

| | | |
|---|---|---|
| EP | 1 961 418 | 8/2008 |
| JP | 2000169321 | 6/2000 |
| JP | 2002284702 | 10/2002 |
| JP | 2008/193572 | 7/2006 |
| WO | WO 1994/005250 | 3/1994 |
| WO | WO 1994/019948 | 9/1994 |
| WO | WO 1997/007230 | 2/1997 |
| WO | WO 1997/026908 | 7/1997 |
| WO | WO 2005/016329 | 2/2005 |
| WO | WO 2006/065736 | 6/2006 |
| WO | WO 2008/070961 | 6/2008 |
| WO | WO 2009/088986 | 7/2009 |
| WO | WO 2010/140902 | 12/2010 |
| WO | WO 2012/010644 | 1/2012 |
| WO | WO 2012/064973 | 5/2012 |
| WO | WO 2013/003601 | 1/2013 |

OTHER PUBLICATIONS

Weber et al. The Journal of Emergency Medicine, 1999, 17 (2), 235-237.*

Zuang et al. Subgroup 2. Skin Irritation/Corrosion, in Cosmetics-European Commission, http://ec.europa.eu/consumers/sectors/cosmetics/files/doc/antest/(5)_chapter_3/2_skin_irritation_en.pdf., accessed Mar. 13, 2014.

Robert et al. New Engl. J. Med. 1999, 341 (24), 1817-1828.

PCT Written Opinion of the International Searching Authority for International Application No. PCT/US12/44660 dated Jul. 15, 2013.

PCT Written Opinion of the International Searching Authority for International Application No. PCT/US12/44593 dated Sep. 7, 2012.

PCT Written Opinion of the International Searching Authority for International Application No. PCT/US12/44628 dated Apr. 5, 2013.

PCT Written Opinion of the International Searching Authority for International Application No. PCT/US13/052307 dated Dec. 5, 2013.

Yehuda et al., Potential skin anti-inflammatory effects of 4-methylthiobutylisothiocyanate (MTBI) isolated from rocket (Eruca Sativa) seeds, Biofactors 35(3), pp. 295-305, 2009. Abstract; p. 297, Fig. 1. https://www.researchgate.net/publication/24443311_Potential_skin_antiinflammatory_effects_of_4-methylthiobutylisothiocyanate_MTBI_from_rocket_Eruca_sativa_seeds.

Valentine W. M. et al.: "Covalent Cross-Linking of Erythrocyte Spectrin by Carbon Disulfide in Vivo," Toxicology and Applied Pharmacology, Academic Press, Amsterdam, NL, vol. 121, No. 1, Jul. 1, 1993 pp. 71-77.

Sundaram G. S. M. et al.: "Synthesis of Bioorthogonal and Crosslinking Amino Acids for Use in Peptide Synthesis," Amino Acids; The Forum for Amino Acid and Protein Research, Springer-Verlag, VI, vol. 39, No. 5, Apr. 22, 2010, pp. 1381-1384.

Mironov et al.: "Synthesis and Properties of New Chlorin and Bacteriochlorin Photosensitizers," Proceedings of SPIE; Photochemistry; Photodynamic Therapy and Other Modalities. vol. 2625, Jan. 31, 1996, pp. 23-32.

Allyl Isothiocyante Product Safety Data Sheet. sc-252361, pp. 1-14.

Office Action for U.S. Appl. No. 13/342,516 dated May 22, 2013.

Office Action for U.S. Appl. No. 13/342,516 dated Mar. 18, 2014.

Office Action for U.S. Appl. No. 14/594,788 dated Sep. 30, 2015.

(56) References Cited

OTHER PUBLICATIONS

Office Action for U.S. Appl. No. 14/594,788 dated May 17, 2016.
Office Action for U.S. Appl. No. 14/880,408 dated Apr. 6, 2016.
Office Action for U.S. Appl. No. 14/880,408 dated Jul. 25, 2016.
Office Action for U.S. Appl. No. 14/880,408 dated Oct. 18, 2016.
Office Action for U.S. Appl. No. 14/880,418 dated Apr. 7, 2016.
Office Action for U.S. Appl. No. 14/880,418 dated Jul. 19, 2016.
Office Action for U.S. Appl. No. 14/880,418 dated Oct. 18, 2016.
Office Action for U.S. Appl. No. 14/880,426 dated Aug. 8, 2016.
Office Action for U.S. Appl. No. 14/880,426 dated Oct. 31, 2016.
Office Action for U.S. Appl. No. 13/348,821 dated Jan. 16, 2013.
Office Action for U.S. Appl. No. 13/348,821 dated Feb. 25, 2014.
Office Action for U.S. Appl. No. 14/519,462 dated Nov. 30, 2015.
Office Action for U.S. Appl. No. 14/519,462 dated Jul. 14, 2016.
Office Action for U.S. Appl. No. 14/868,897 dated Jun. 27, 2016.
Office Action for U.S. Appl. No. 14/868,929 dated Jul. 7, 2016.
Office Action for U.S. Appl. No. 14/868,959 dated Jul. 7, 2016.
Office Action for U.S. Appl. No. 13/952,236 dated Jun. 23, 2016.
Office Action for U.S. Appl. No. 14/519,510 dated Oct. 16, 2015.
Office Action for U.S. Appl. No. 14/519,510 dated Jun. 8, 2016.
Office Action for U.S. Appl. No. 14/867,585 dated Aug. 18, 2016.
Office Action for U.S. Appl. No. 14/867,626 dated Aug. 19, 2016.
Office Action for U.S. Appl. No. 13/351,616 dated Jan. 17, 2012.
Office Action for U.S. Appl. No. 13/351,616 dated Sep. 18, 2014.
Office Action for U.S. Appl. No. 13/351,616 dated Jan. 29, 2016.

* cited by examiner

LYSINE DERIVATIVE HAVING AN ISOTHIOCYANATE FUNCTIONAL GROUP AND ASSOCIATED METHOD OF USE

CROSS-REFERENCE TO RELATED APPLICATIONS

This application is a continuation of U.S. application Ser. No. 14/594,788, entitled "METHOD FOR TREATING PHYTOPHOTODERMATITIS," filed Jan. 12, 2015, which is a continuation of U.S. application Ser. No. 13/342,516, entitled "METHOD FOR TREATING PHYTOPHOTODERMATITIS," filed Jan. 3, 2012, now U.S. Pat. No. 8,933,119, which claims the benefit of U.S. Provisional Application Ser. No. 61/429,325, entitled "METHOD FOR TREATING PHYTOPHOTODERMATITIS," filed Jan. 3, 2011 and U.S. Provisional Application Ser. No. 61/502,067, entitled "METHOD FOR TREATING PHYTOPHOTODERMATITIS," filed Jun. 28, 2011—all of which are hereby incorporated herein by reference in their entirety, including all references cited therein.

BACKGROUND OF THE INVENTION

1. Field of the Invention

The present invention relates in general to a method for treating phytophotodermatitis and, more particularly, to a method for treating phytophotodermatitis caused by exposure to linear and/or non-linear (e.g., angular) furanocoumarins and derivatives thereof—among other chemical compounds.

2. Background Art

Phytophotodermatitis (hereinafter sometimes referred to "PPD") is traditionally expressed as a cutaneous phototoxic inflammatory response and/or eruption resulting from exposure to one or more photosensitizing, chemical compounds (e.g., botanical substances) and electromagnetic radiation (e.g., ultraviolet (UV) radiation) emanating primarily from the sun.

The photosensitizing, chemical compounds or skin toxins that result in human phytophotodermatitis are traditionally produced by members of several plant families including, but not limited to, Umbelliferae, Leguminosae, Apiaceae, Rutaceae, Moraceae, Roasceae, Asteraceae, Brassicaceae, Clusiaceae, Convolvulaceae, Anacardiaceae, Fabaceae, and Ranunculaceae. Common plants implicated in these families include, but are not limited to, celery, giant hogweed, *angelica*, parsnip, fennel, dill, anise, parsley, lime, lemon, rue, fig, mustard, scurf pea, and chrysanthemums—just to name a few. Notably, giant hogweed is so problematic that the United States Government regulates it as a federal noxious weed.

Among the skin toxins produced by plants in the above-identified plant families are furanocoumarins including, but not limited to, psoralen, 8-isopentenyloxypsoralen (imperatorin), 5-hydroxypsoralen (bergaptol), 5-methoxypsoralen (5-MOP), 8-hydroxypsoralen (xanthotoxol), 8-methoxypsoralen (8-MOP), 5,8-dihydroxypsoralen, 5,8-dimethoxypsoralen (isopimpinellin), angelicin, and sphondin. Chemical structures of non-limiting, representative furanocoumarins are provided below.

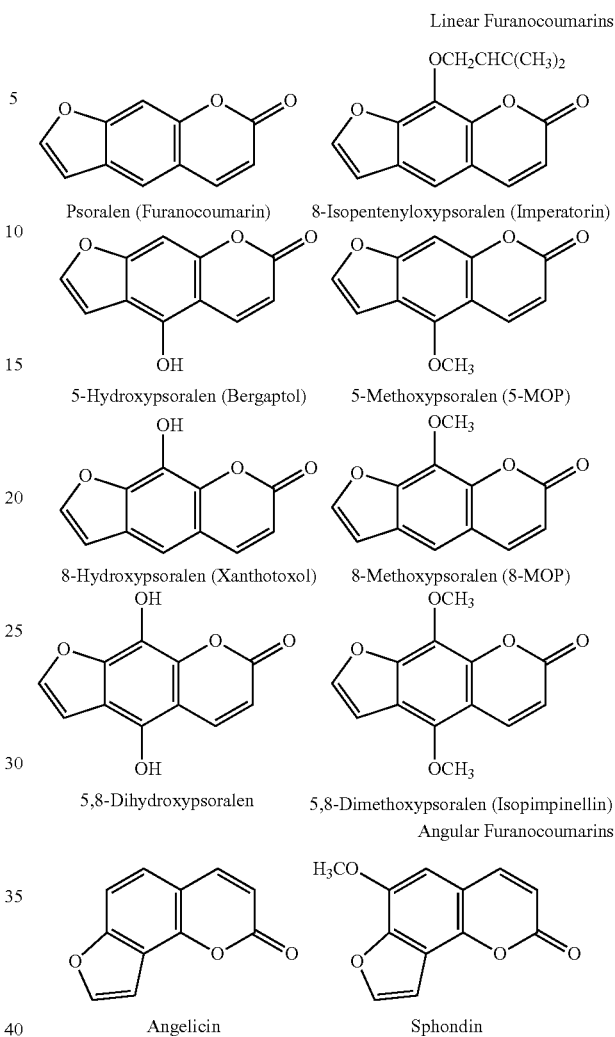

It is believed that exposure to electromagnetic radiation, such as UV-A light enables furanocoumarins to absorb energy, thereby altering reactivity of their molecular structures, as well as attain activated, high-energy states. In the presence of oxygen, activated molecules are believed to form photoaddition products with DNA pyrimidine bases via DNA interstrand crosslinking at cytosine and thymidine with the furan ring of the furanocoumarins, which results in epidermal cell nucleic damage. In the absence of oxygen, activated furanocoumarins are also believed to produce oxygen, superoxides, and hydroxy radicals, which are believed cause cellular membrane damage.

Responses and/or eruptions from PPD typically begin approximately 24 hours after exposure and peak between approximately 48 hours and approximately 72 hours after exposure. Phytophotodermatitis normally manifests as a burning erythema that is often followed by blistering, epidermal necrosis, and/or desquamation. Postinflammatory hyperpigmentation lasting weeks to several months typically follows the acute response and/or eruption from PPD. Affected areas often remain hypersensitive to UV radiation for many years and re-eruptions of lesions and blisters is common.

Until now, the only known antidote for contact with and/or exposure to these skin toxins was to immediately wash the skin thoroughly with soap and water, thereby removing at least some of the toxins and hopefully minimizing any reaction with subsequent exposure to sunlight. Unfortunately, the average victim is usually not aware of exposure to the photosensitizing, chemical compounds until a response and/or eruption occurs and problematic symptoms begin to manifest. Once this has occurred, washing with soap and water is ineffective and potentially contraindicated for certain reactions—likely because the plant toxins have penetrated into the epidermis and/or dermis. Currently, it is recommended that once problematic symptoms begin to manifest, professional medical advice should be sought immediately because medical treatment with prescription topical steroids may reduce the severity of a person's reaction. It is further currently recommended to cover any burns and blisters with sterile dressings to prevent infection, and to wear clothing that shields the skin from sunlight. Long-term, use of sun block in subsequent years and the wearing of sun protective clothing may be required to prevent sensitization by sunlight.

While the above-identified medical treatments do appear to provide at least some relief to those who are afflicted by phytophotodermatitis, such treatment remains non-desirous and/or problematic inasmuch as, among other things, none of the above-identified treatments provide sufficient therapeutic relief from the debilitating effects of PPD.

It is therefore an object of the present invention to provide a method for treating phytophotodermatitis which offers timely relief from the symptoms presented when one is afflicted with PPD.

These and other objects of the present invention will become apparent in light of the present specification, claims, and drawings.

SUMMARY OF THE INVENTION

In one embodiment, the present invention is directed to a method for treating phytophotodermatitis comprising the step of: applying an isothiocyanate functional surfactant to an area affected by phytophotodermatitis, wherein said isothiocyanate functional surfactant comprises at least one isothiocyanate functional group associated with an aliphatic and/or aromatic carbon atom of the isothiocyanate functional surfactant.

In another embodiment of the present invention, the method for treating phytophotodermatitis further comprises the step of removing the isothiocyanate functional surfactant from the area affected by phytophotodermatitis.

In yet another exemplary embodiment, the present invention is directed to a method for treating phytophotodermatitis comprising the steps of: (a) applying an isothiocyanate functional surfactant to an area affected by phytophotodermatitis, wherein said isothiocyanate functional surfactant comprises at least one isothiocyanate functional group associated with an aliphatic and/or aromatic carbon atom of the isothiocyanate functional surfactant; (b) removing the isothiocyanate functional surfactant from the area affected by phytophotodermatitis; and (c) repeating the steps of applying and removing the isothiocyanate functional surfactant to/from the affected area.

The present invention is also directed to a method for treating phytophotodermatitis comprising the step of: washing an area affected by phytophotodermatitis with an isothiocyanate functional surfactant, wherein said isothiocyanate functional surfactant comprises at least one isothiocyanate functional group associated with an aliphatic and/or aromatic carbon atom of the isothiocyanate functional surfactant.

The present invention is further directed to a method for treating phytophotodermatitis comprising the step of: applying a lysine derivative to an area affected by phytophotodermatitis, wherein the lysine derivative comprises an α-nitrogen and a ε-nitrogen, and wherein an alkyl and/or alkanoyl substituent comprising at least approximately 8 carbon atoms is associated with the α-nitrogen, and further wherein at least one isothiocyanate functional group is associated with the ε-nitrogen.

The present invention is still further directed to a method for treating phytophotodermatitis comprising the step of: applying a surfactant to an area affected by phytophotodermatitis, wherein the protonated form of said surfactant is represented by the following chemical structure:

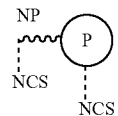

wherein the surfactant comprises a non-polar moiety (NP) and a polar moiety (P), and wherein at least one isothiocyanate functional group (NCS) is associated with the polar and/or non-polar moiety.

In another embodiment, the present invention is directed to a method for treating phytophotodermatitis, comprising the step of: applying a surfactant or a pharmaceutically acceptable salt thereof to an area affected by phytophotodermatitis, wherein the protonated form of said surfactant is represented by the following chemical structure:

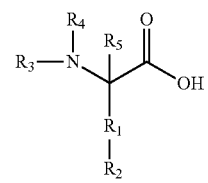

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; and wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s).

The present invention is also directed to a method for treating phytophotodermatitis comprising the step of: applying a surfactant or a pharmaceutically acceptable salt thereof to an area affected by phytophotodermatitis, wherein the protonated form of said surfactant is represented by the following chemical structure:

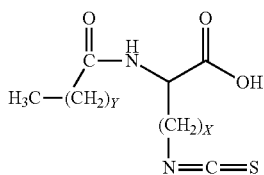

wherein X comprises an integer ranging from approximately 1 to approximately 25, and wherein Y comprises an integer ranging from approximately 6 to approximately 25.

In a preferred embodiment, the present invention is directed to a method for treating phytophotodermatitis comprising the step of: applying a surfactant or a pharmaceutically acceptable salt thereof to an area affected by phytophotodermatitis, wherein the protonated form of said surfactant is represented by the following chemical structure:

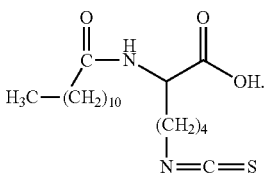

In another embodiment, the present invention is directed to a method for treating phytophotodermatitis, comprising the step of: applying a surfactant or a pharmaceutically acceptable salt thereof to an area affected by phytophotodermatitis, wherein the protonated form of said surfactant is represented by the following chemical structure:

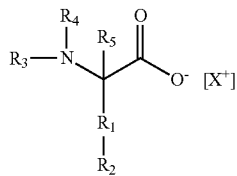

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s), wherein X comprises a counter cation such as, but not limited to, alkali metals, alkaline earth metals, transition metals, s-block metals, d-block metals, p-block metals, $NZ_4^+$, wherein Z comprises, H, $R_6$, $OR_6$, and wherein $R_6$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer.

In yet another preferred embodiment, the present invention is directed to a method for treating phytophotodermatitis as disclosed supra, further comprising the step of applying an additional surfactant, wherein the additional surfactant is selected from at least one of the group comprising a non-ionic surfactant, an anionic surfactant, a cationic surfactant, a zwitterionic surfactant, and combinations thereof.

DETAILED DESCRIPTION OF THE INVENTION

While this invention is susceptible of embodiment in many different forms, there is shown in the drawings and described herein in detail several specific embodiments with the understanding that the present disclosure is to be considered as an exemplification of the principles of the invention and is not intended to limit the invention to the embodiments illustrated.

In accordance with the present invention, methods for treating phytophotodermatitis are provided herein. In particular, methods for treating phytophotodermatitis preferably caused by exposure to linear and/or non-linear (e.g., angular) furanocoumarins and derivatives thereof are disclosed. Non-limiting examples of linear furanocoumarins include psoralen, 8-isopentenyloxypsoralen (imperatorin), 5-hydroxypsoralen (bergaptol), 5-methoxypsoralen (5-MOP), 8-hydroxypsoralen (xanthotoxol), 8-methoxypsoralen (8-MOP), 5,8-dihydroxypsoralen, and 5,8-dimethoxypsoralen (isopimpinellin). Non-limiting examples of angular furanocoumarins include angelicin and sphondin. As briefly discussed supra, the photosensitizing, chemical compounds and/or skin toxins that result in phytophotodermatitis are traditionally produced by members of several plant families including, but not limited to, Umbelliferae, Leguminosae, Apiaceae, Rutaceae, Moraceae, Roasceae, Asteraceae, Brassicaceae, Clusiaceae, Convolvulaceae, Anacardiaceae, Fabaceae, and Ranunculaceae. Indeed, common plants implicated in these families include, but are not limited to, celery, giant hogweed, *angelica*, parsnip, fennel, dill, anise, parsley, lime, lemon, rue, fig, mustard, scurf pea, and chrysanthemums—just to name a few. It will be understood that phytophotodermatitis caused by exposure to giant hogweed (i.e., *Heracleum mantegazzianum*) is particularly problematic in the United States. While methods for treating phytophotodermatitis caused by exposure to linear and/or non-linear (e.g., angular) furanocoumarins are disclosed in detail herein, it will be understood that methods for treating phytophotodermatitis caused by exposure to other photosensitizing, chemical compounds are likewise contemplated for use in accordance with the present invention.

In one embodiment, the present invention is directed to a method for treating phytophotodermatitis comprising the steps of applying one or more isothiocyanate functional surfactants to an area affected by phytophotodermatitis. Preferably, the isothiocyanate functional surfactant comprises one or more isothiocyanate functional groups associated with and/or directly associated with an aliphatic and/or aromatic carbon atom of the isothiocyanate functional surfactant. It will be understood that an area affected by phytophotodermatitis may comprise areas proximate and/or contiguous to areas where a manifestation of physical symptoms are present. Physical symptoms include, for example, discomfort, itching, burning, erythema, blistering, epidermal necrosis, desquamation, discoloration, and/or hyperpigmentation—just to name a few. It will be further understood that isothiocyanate functional surfactants, regardless of their ordinary meaning, are defined herein as a surfactant having an isothiocyanate functional group associated therewith. It will be yet further understood that the term associated as applied to chemical contexts, regardless of its ordinary meaning, is defined herein as attached, a covalent bond, a polar covalent bond, an ionic bond, a hydrogen bond, van der Waals forces, electrostatic interaction, etcetera.

The term surfactant derives from contraction of the terms surface-active-agent and is defined herein as a molecule and/or group of molecules which are able to modify the interfacial properties of the liquids (aqueous and non-aqueous) in which they are present. The surfactant properties of these molecules reside in their amphiphilic character which stems from the fact that each surfactant molecule has both a hydrophilic moiety and a hydrophobic (or lipophilic) moiety, and that the extent of each of these moieties is balanced so that at concentrations at or below the critical micelle concentration (i.e., CMC) they generally concentrate at the air-liquid interface and materially decrease the interfacial tension. For example, sodium salts of saturated carboxylic acids are extremely soluble in water up to C8 length and are thus not true surfactants. They become less soluble in water from C9 up to C18 length, the domain of effective surfactants for this class of compounds. The carboxylic acids (fatty acids) can be either saturated or unsaturated starting from C16 chain lengths.

Without being bound by any one particular theory, it is believed that the isothiocyanate functional surfactants disclosed herein facilitate treatment of numerous forms of phytophotodermatitis by boosting the body's immune system. It is also believed that the isothiocyanate functional surfactants disclosed herein facilitate elevating phase II enzymes (e.g., HAD(P)H quinine oxidoreductase) which are believed to, among other things regulate inflammatory responses within the body, as well as detoxify carcinogens and activated carcinogens.

In accordance with the present invention, the isothiocyanate functional surfactants may be used as a topical leave-on product in which one or more surfactants remain on the skin and are not immediately and/or ever rinsed off away from the skin. Alternatively, the isothiocyanate functional surfactants of the present invention may be used as a topical wash in an apply-and-rinse fashion. For either case, it is preferred that the isothiocyanate functional surfactants be generally mild to human skin (e.g., non-irritating or low-irritating). In particular, anionic N-alkanoyl surfactants derived from amino acids are especially preferred because, while not completely predictable, they have a tendency to be mild. The methods of preparation detailed in this invention employ but are not limited to amino acids that possess at least two amine functionalities, at least one of which is converted to an N-alkanoyl functionality, and at least one of which is converted into isothiocyanate functionality. The amino acids include but are not limited to $\alpha$-amino acids lysine, ornithine, 2,4-diaminobutanoic acid, 2,3-diaminopropionic acid, 2,7-diaminoheptanoic acid, and 2,8-diaminooctanoic acid. Additionally, amino acids other than $\alpha$-amino acids may be employed, such as $\beta$-amino acids, etcetera. It will be understood that amino acid derived surfactants are preferred due to their mild nature, but any one of a number of other surfactants are likewise contemplated for use in accordance with the present invention.

Method for preparing isothiocyanate functional surfactants and/or their precursors can involve but is not limited to conversion of an amine functionality to an isothiocyanate functionality. The method of conversion of amine functionalities to isothiocyanate functionalities can be, but is not limited to: (1) reaction with carbon disulfide to yield an intermediate dithiocarbamate, followed by reaction with ethylchloroformate or its functional equivalent such as bis (trichloromethyl)-carbonate, trichloromethyl chloroformate, or phosgene; (2) reaction with thiophosgene; (3) reaction with 1,1'-thiocarbonyldiimidizole; (4) reaction with phenylthiochloroformate; (5) reaction with ammonium or alkali metal thiocyanate to prepare an intermediate thiourea followed by cleaving to the isothiocyanate via heating; and (6) reaction with an isothiocyanato acyl halide [SCN—$(CH_2)_n$—CO—Cl]. The resulting isothiocyanate functional surfactant, depending on the method of preparation, can be isolated as a pure material or as a mixture with other surfactants. The resulting isothiocyanate functional surfactant, depending on the method of preparation, can be isolated and used directly in nonionic form, anionic form, cationic form, zwitterionic (amphoteric) form, or in a neutral surfactant-precursor form in combination with a base such as sodium hydroxide or triethanol amine if the neutral surfactant-precursor form possesses a protonated carboxylic acid group such that reaction (deprotonation) with the base converts the neutral surfactant-precursor form to an anionic surfactant, or in neutral surfactant-precursor form in combination with an acid if the neutral surfactant-precursor form possess amine functionality such that reaction (protonation) with the acid converts the neutral surfactant-precursor form to a cationic surfactant.

In accordance with the present invention the step of applying comprises, but is not limited to, spraying, dripping, dabbing, rubbing, blotting, dipping, and any combination thereof.

In a preferred embodiment of the present invention, the isothiocyanate functional surfactant is removed from the affected area after a period of time. Such a period comprises, but is not limited to, seconds (e.g., 1 second, 2 seconds, 5 seconds, 10 seconds, 15 seconds, 20 seconds, 30 seconds, 45 seconds, and 60 seconds), minutes (e.g. 1 minutes, 2 minutes, 5 minutes, 10 minutes, 15 minutes, 20 minutes, 30 minutes, 45 minutes, and 60 minutes), hours (e.g. 1 hour, 2 hours, 5 hours, 10 hours, 15 hours, 20 hours, 30 hours, 45 hours, and 60 hours), days (e.g. 1 day, 2 days, 3 days, 4 days, 5 days, 6 days, 7 days, 10 days, 14 days, 21 days, 30 days), etcetera. It will be understood that the step of removing preferably occurs via rinsing, wiping, and/or extracting—just to name a few.

Depending upon the subject and/or the severity of the phytophotodermatitis, multiple applications may be necessary. As such, the steps of applying and/or removing the isothiocyanate functional surfactant may be repeated one or a plurality of times.

The present invention is also directed to a method for treating phytophotodermatitis comprising the steps of applying a lysine derivative to an area affected by phytophotodermatitis, wherein the lysine derivative comprises an α-nitrogen and a ε-nitrogen. Preferably, an alkyl substituent comprising at least approximately 8 carbon atoms is associated with the α-nitrogen. Preferably, at least one isothiocyanate functional group is associated with the ε-nitrogen.

The present invention is further directed to a method for treating phytophotodermatitis comprising the steps of: applying a surfactant to an area affected by phytophotodermatitis, wherein the surfactant is represented by the following chemical structure:

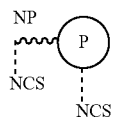

and wherein the surfactant comprises a non-polar moiety (NP) and a polar moiety (P), and wherein at least one isothiocyanate functional group (NCS) is associated with the polar and/or non-polar moiety.

The present invention is yet further directed to a method for treating phytophotodermatitis, comprising the step of: applying a surfactant or a pharmaceutically acceptable salt thereof to an area affected by phytophotodermatitis, wherein the protonated form of said surfactant is represented by the following chemical structure:

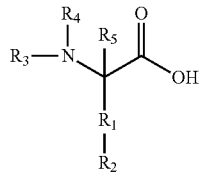

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; and wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s).

In this embodiment, the surfactant is preferably represented by the following chemical structure:

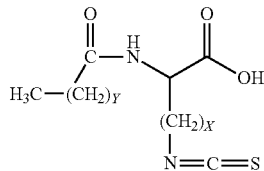

wherein X comprises an integer ranging from approximately 1 to approximately 25, and wherein Y comprises an integer ranging from approximately 6 to approximately 25.

More preferably, the surfactant is represented by the following chemical structure:

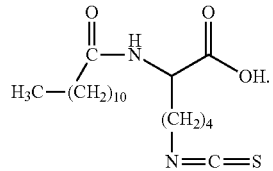

In another embodiment, the present invention is directed to a method for treating phytophotodermatitis, comprising the step of: applying a surfactant or a pharmaceutically acceptable salt thereof to an area affected by phytophotodermatitis, wherein the protonated form of said surfactant is represented by the following chemical structure:

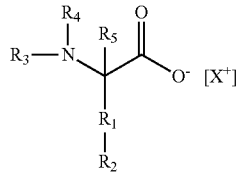

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s), wherein X comprises a counter cation such as, but not limited to, alkali metals, alkaline earth metals, transition metals, s-block metals, d-block metals, p-block metals, $NZ_4^+$, wherein Z comprises, H, $R_6$, $OR_6$, and wherein $R_6$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer.

In accordance with the present invention, the isothiocyanate functional surfactant may also be associated with an additional surfactant, wherein the additional surfactant is selected from at least one of the group comprising a non-ionic surfactant, an anionic surfactant, a cationic surfactant, a zwitterionic surfactant, and combinations thereof.

Non-limiting examples of preferred anionic surfactants include taurates; isethionates; alkyl and alkyl ether sulfates; succinamates; alkyl sulfonates, alkylaryl sulfonates; olefin sulfonates; alkoxy alkane sulfonates; sodium and potassium salts of fatty acids derived from natural plant or animal sources or synthetically prepared; sodium, potassium, ammonium, and alkylated ammonium salts of alkylated and acylated amino acids and peptides; alkylated sulfoacetates; alkylated sulfosuccinates; acylglyceride sulfonates, alkoxyether sulfonates; phosphoric acid esters; phospholipids; and combinations thereof. Specific anionic surfactants contemplated for use include, but are by no means limited to, ammonium cocoyl isethionate, sodium cocoyl isethionate, sodium lauroyl isethionate, sodium stearoyl isethionate, sodium lauroyl sarcosinate, sodium cocoyl sarcosinate, sodium lauryl sarcosinate, disodium laureth sulfosuccinate, sodium lauryl sulfoacetate, sodium cocoyl glutamate, TEA-cocoyl glutamate, TEA cocoyl alaninate, sodium cocoyl taurate, potassium cetyl phosphate.

Non-limiting examples of preferred cationic surfactants include alkylated quaternary ammonium salts $R_4NX$; alkylated amino-amides $(RCONH-(CH_2)_n)NR_3X$; alkylimidazolines; alkoxylated amines; and combinations thereof. Specific examples of anionic surfactants contemplated for use include, but are by no means limited to, cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, distearyl methyl ammonium chloride, distearyl methyl ammonium bromide, ditallow dimethyl ammonium chloride, ditallow dimethyl ammonium sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-imonium chloride phosphate, stearamidopropyl ethyldimonium ethosulfate, stearimidopropyldimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, ditallowyl oxyethyl dimethyl ammonium chloride, behenamidopropyl PG dimonium chloride, dilauryl dimethyl ammonium chloride, distearly dimethyl ammonium chloride, dimyristyl dimethyl ammonium chloride, dipalmityl dimethyl ammonium chloride, distearyl dimethyl ammonium chloride, stearamidoproyl PG-dimonium chloride phosphate, stearamidopropyl ethyldiammonium ethosulfate, stearamidopropyl dimethyl (myristyl acetate) ammonium chloride, stearimidopropyl dimethyl cetaryl ammonium tosylate, stearamido propyl dimethyl ammonium chloride, stearamidopropyl dimethyl ammonium lactate.

Non-limiting examples of preferred non-ionic surfactants include alcohols, alkanolamides, amine oxides, esters (including glycerides, ethoxylated glycerides, polyglyceryl esters, sorbitan esters, carbohydrate esters, ethoxylated carboxylic acids, phosphoric acid triesters), ethers (including ethoxylated alcohols, alkyl glucosides, ethoxylated polypropylene oxide ethers, alkylated polyethylene oxides, alkylated polypropylene oxides, alkylated PEG/PPO copolymers), silicone copolyols. Specific examples of non-ionic surfactants contemplated for use include, but are by no means limited to, cetearyl alcohol, ceteareth-20, nonoxynol-9, C12-15 pareth-9, POE(4) lauryl ether, cocamide DEA, glycol distearate, glyceryl stearate, PEG-100 stearate, sorbitan stearate, PEG-8 laurate, polyglyceryl-10 trilaurate, lauryl glucoside, octylphenoxy-polyethoxyethanol, PEG-4 laurate, polyglyceryl diisostearate, polysorbate-60, PEG-200 isostearyl palmitate, sorbitan monooleate, polysorbate-80.

Non-limiting examples of preferred zwitterionic or amphoteric surfactants include betaines; sultaines; hydroxysultaines, amido betaines, amidosulfo betaines; and combinations thereof. Specific examples of amphoteric surfactants contemplated for use include, but are by no means limited to, cocoamidopropyl sultaine, cocoamidopropyl hydroxyl sultaine, cocoamidopropylbetaine, coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl (2-bishydroxy) carboxymethyl betaine, stearyl bis-(2-hydroxyethyl) carboxymethyl betaine, oleyl dimethyl gamma-carboxypropyl betaine, lauryl bis-(2-hydroxypropyl)alpha carboxymethyl betaine, coco dimethyl sulfopropyl betaine, stearyl dimethyl sulfopropyl betaine, lauryl dimethyl sulfoethyl betaine, lauryl bis(2-hydroxyethyl) sulfopropyl betaine, oleyl betaine, cocamidopropyl betaine.

The invention is further described by the following examples.

Example I

Preparation of a mixture of $N_\alpha$-lauroyl-$N_\epsilon$-isothiocyanato-L-Lysine with $N_\alpha,N_\epsilon$-bis-lauroyl-L-lysine A 1 liter beaker equipped with an overhead mechanical stainless steel paddle stirrer was charged with 100 mL of 1 M NaOH (0.100 mol). Stirring was begun and the beaker cooled to −5° C. to −10° C. using a salt/ice bath. Next, 23.4 g (0.100 mol) of $N_\epsilon$-benzylidene-L-lysine (prepared via the method of Bezas, B and Zervas, L., JACS, 83, 1961, 719-722) was added. Immediately afterward and while keeping the solution cold, 140 mL (0.140 mol) of precooled (in a salt/ice bath) 1 M NaOH and 26.1 mL of lauroyl chloride was added in two equal portions over a period of 6 minutes. The mixture was stirred for 10 more minutes at −5 to −10° C., then the ice bath was removed and the reaction mixture allowed to stir for another 1 hour while warming to room temperature. Next, the reaction mixture was cooled using a salt/ice bath and then sufficient concentrated HCl was added to adjust the pH to 7.5-7.8. With the pH at 7.8-7.8 and with continued cooling and stirring, 4.6 mL (60% of stoichiometric, 0.068 mol) of thiophosgene was added dropwise via an additional funnel over the period of 1 hour. During this time, sufficient 1 M NaOH was added to maintain a pH range between 7.5-7.8. After the thiophosgene addition was complete, additional 1 M NaOH was added as necessary until the pH stabilized in 7.5-7.8 range. Next, sufficient 30% NaOH was added to adjust the pH to approximately 8.5. Next, 12 mL (0.051 mol) of lauroyl chloride was rapidly added, followed by sufficient 1 M NaOH to keep the pH in the range of 8.00-8.50. Next, sufficient concentrated HCl was added to adjust the pH to 1.5. The reaction mixture was filtered via vacuum filtration, and the precipitate washed with dilute HCl (pH=2). The product, a white moist solid, was dried in vacuo while heating to 60° C. 45.19 g of white solid product was recovered, a mixture of predominantly $N_\alpha$-lauroyl-$N_\epsilon$-isothiocyanato-L-lysine and $N_\alpha,N_\epsilon$-bis-lauroyl-L-lysine (determined via LC-MS analysis). Both compounds in this mixture can be simultaneously converted into anionic (carboxylate) surfactants via reaction with aqueous NaOH to yield a clear aqueous solution of the surfactants.

Example II

Preparation of Pure $N_\alpha$-lauroyl-$N_\epsilon$-isothiocyanato-L-Lysine

Step 1: Preparation of $N_\alpha$-lauroyl-$N_\epsilon$-carbobenzoxy-L-Lysine 60.0 g of $N_\epsilon$-cbz-L-Lysine (cbz is carbobenzoxy) purchased from Atomole Scientific Company, LTD was added to a three-liter beaker along with 1200 mL of RO water and the mixture was stirred. Next, 39 mL of 30% aqueous NaOH was added, resulting in dissolution of the $N_\epsilon$-cbz-L-Lysine. The resulting solution was cooled in an ice bath and then 52.5 mL of lauroyl chloride was added. The ice bath was removed 30 minutes later, and stirring continued for an additional six hours, at which time 18 mL of concentrated hydrochloric acid was added. The reaction mixture was then filtered via vacuum filtration, the white solid product washed with 1 M aqueous HCl, and then the solid product was dried in vacuo while heated to approximately 85° C. 96.5 g of dry white solid product was obtained. The product can be further purified by dissolving it in methanol, filtering off any insoluble precipitate, and removing the methanol in vacuo to recover a white solid product (mp 99.5-103.0° C.)

Step 2: Preparation of $N_\alpha$-lauroyl-$N_\epsilon$-ammonium chloride-L-Lysine 10.0 g of $N_\alpha$-lauroyl-$N_\epsilon$-carbobenzoxy-L-Lysine was weighed into a one liter Erlenmeyer flask equipped with a magnetic stir bar. 150 mL of concentrated hydrochloric acid was added and the solution was stirred and heated in an oil bath to 104° C., then allowed to cool with the oil bath back to room temperature. The solution was then cooled to 9° C. for approximately four hours, during which time a large mass of white precipitate formed. The reaction mixture was filtered in vacuo and rinsed with a small amount of cold 1 M HCl. The white solid reaction product was then dried in vacuo while being heated to 78° C., yielding 7.89 g of white solid product (mp 191-193° C.).

Step 3: Preparation of $N_\alpha$-lauroyl-$N_\epsilon$-isothiocyanato-L-Lysine 0.46 mL of thiophosgene was added to 30 mL of dichloromethane in a 125 mL Erlenmeyer flask equipped with a magnetic stir bar. To this solution was drop wise added over 15 minutes a solution consisting of 2.00 g $N_\alpha$-lauroyl-$N_\epsilon$-ammonium chloride-L-Lysine, 10 mL RO water, and 2.7 mL 20% aqueous NaOH. Stirring was continued for an additional 30 minutes, after which sufficient concentrated hydrochloric acid was added to lower the pH to 1 as indicated by testing with pHydrion paper. The reaction solution was then transferred into a separatory funnel and the bottom turbid dichloromethane layer was isolated and dried with anhydrous magnesium sulfate and gravity filtered. To the filtrate was added 50 mL of hexanes. The solution was then concentrated via removal of 34 mL of solvent via trap-to-trap distillation and then placed in a −19° C. freezer. A mass of white precipitate formed after a few hours and was isolated via vacuum filtration and then dried in vacuo for 2 hours. 1.130 g of a slightly off white solid powder product was obtained [mp 37.0-39.0° C.; IR (cm$^{-1}$), 3301sb, 2923s, 2852s, 2184m, 2099s, 1721s, 1650s, 1531s, 1456m, 1416w, 1347m, 1216m, 1136w]

Example III

Preparation of a Two-Part Formulation for the Treatment of Phytophotodermatitis A two-part formulation for topical application to the skin was prepared as follows:

Part I: A 25% by mass mixture of $N_\alpha$-lauroyl-$N_\epsilon$-isothiocyanato-L-Lysine in Dow Corning DC344 fluid (a mixture of octamethyl-cyclotetrasiloxane and decamethyl-cyclopentasiloxane) was prepared in a mortar and pestle to produce a paste that was loaded into a 5 ml plastic disposable syringe. A syringe needle was not employed. Rather, the dispensing end of the syringe was capped except for when dispensing without a syringe needle into the palm of a hand occurred.

Part II: Part II consisted of Cetaphil Moisturizing Lotion to which additional triethanol amine (TEA) was added such that the concentration of the additional triethanol amine was 0.006 g triethanol amine per gram of lotion, raising the pH of the Cetaphil Lotion from 7.74 to 8.77.

Preferred Instructions for Application of Formulation to the Skin: A 0.2 mL portion of the $N_\alpha$-lauroyl-$N_\epsilon$-isothiocyanato-L-Lysine/DC344 mixture is dispensed from the syringe into the palm of a hand (approximately 0.13 g of the mixture). Next, two full squirts of the Cetaphil/TEA lotion is dispensed on top of the $N_\alpha$-lauroyl-$N_\epsilon$-isothiocyanato-L-Lysine/DC344 mixture (approximately 2.8 g of the lotion). Next, using the index finger of the other hand, the components are mixed thoroughly for 30 seconds, during which time the water insoluble $N_\alpha$-lauroyl-$N_\epsilon$-isothiocyanato-L-Lysine surfactant-precursor is deprotonated to yield the water-soluble anionic (carboxylate) surfactant and yield a homogenous smooth white lotion (this reduces the pH to 7.4). This mixture is then applied to the afflicted areas by gently rubbing it on as one would apply any moisturizing lotion. Treatment is recommended two to three times per day until the symptoms of the phytophotodermatitis subside.

Example IV

Preparation of a One-Part Formulation for the Treatment of Phytophotodermatitis

A one-part formulation for topical application to the skin was prepared as follows:

First, 0.00025% (by wt.; 5.0 micromolar) of Sodium $N_\alpha$-lauroyl-$N_\epsilon$-isothiocyanate-L-Lysinate, the sodium salt of the material provided in step three of Example II, was mixed with 2% Lauryl PEG-10 Methyl Ether Dimethicone (commercially available from Clear Chemical Corporation, Holland, Mich.) which was QS to achieve 100% with 2,6,10,15,19,23-Hexamethyltetracosane (commercially available from Sigma-Aldrich). It will be understood that the concentration of Sodium $N_\alpha$-lauroyl-$N_\epsilon$-isothiocyanate-L-Lysinate may range from approximately 0.000001% to approximately 50%. Non-limiting examples of additional concentrations include 0.0005%, 0.005%, 0.005%, 0.005%, 0.05%, 0.5%, 5% —just to name a few. It will be further understood that the concentration of Lauryl PEG-10 Methyl Ether Dimethicone may range from approximately 0.000001% to approximately 50%.

Preferred Instructions for Application of the One-Part Formulation to the Skin: A 0.1-1.0 mL portion of the one-part formulation is dispensed from a container into the palm of a hand for subsequent administration to an affected area and/or is dispensed directly onto an affected area by gently rubbing it on as one would apply a moisturizing lotion. Treatment is recommended one to four times per day until the symptoms of the phytophotodermatitis subside.

The foregoing description merely explains and illustrates the invention and the invention is not limited thereto except insofar as the appended claims are so limited, as those skilled in the art who have the disclosure before them will be able to make modifications without departing from the scope of the invention.

What is claimed and desired to be secured by Letters Patent of the United States is:

1. A method for treating phytophotodermatitis with a lysine derivative surfactant having an isothiocyanate functional group, comprising the step(s) of:
    applying a lysine derivative surfactant to an area affected by phytophotodermatitis, wherein the lysine derivative surfactant comprises an alkyl and/or alkanoyl substituent containing at least 8 carbon atoms bound to the α-nitrogen of the lysine, and further wherein the ε-nitrogen of the lysine forms part of an isothiocyanate functional group.

2. The method according to claim 1, further comprising the step of applying an additional surfactant, wherein the additional surfactant is selected from at least one of the group comprising a non-ionic surfactant, an anionic surfactant, a cationic surfactant, a zwitterionic surfactant, and combinations thereof.

3. The method according to claim 1, further comprising the step of applying an additional surfactant, wherein the additional surfactant comprises a non-ionic surfactant.

4. The method according to claim 1, further comprising the step of applying an additional surfactant, wherein the additional surfactant comprises an anionic surfactant.

5. The method according to claim 1, further comprising the step of applying an additional surfactant, wherein the additional surfactant comprises a cationic surfactant.

6. The method according to claim 1, further comprising the step of applying an additional surfactant, wherein the additional surfactant comprises a zwitterionic surfactant.

7. A method for treating phytophotodermatitis with a lysine derivative surfactant having an isothiocyanate functional group, consisting essentially of the step of:
    applying a lysine derivative surfactant to an area affected by phytophotodermatitis, wherein the lysine derivative surfactant comprises an alkyl and/or alkanoyl substituent containing at least 8 carbon atoms bound to the α-nitrogen of the lysine, and further wherein the ε-nitrogen of the lysine forms part of an isothiocyanate functional group.

8. A method for treating phytophotodermatitis with a lysine derivative surfactant having an isothiocyanate functional group, consisting of the step of:
    applying a lysine derivative surfactant to an area affected by phytophotodermatitis, wherein the lysine derivative surfactant comprises an alkyl and/or alkanoyl substituent containing at least 8 carbon atoms bound to the α-nitrogen of the lysine, and further wherein the ε-nitrogen of the lysine forms part of an isothiocyanate functional group.

* * * * *